(12) United States Patent
Shah et al.

(10) Patent No.: US 11,622,737 B2
(45) Date of Patent: Apr. 11, 2023

(54) RADIOLABELED CELL TRACKING AND IMAGING

(71) Applicant: Siemens Medical Solutions USA, Inc., Malvern, PA (US)

(72) Inventors: Vijay Shah, Knoxville, TN (US); Sven Zuehlsdorff, Knoxville, TN (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 19 days.

(21) Appl. No.: 16/947,144

(22) Filed: Jul. 21, 2020

(65) Prior Publication Data

US 2022/0022826 A1    Jan. 27, 2022

(51) Int. Cl.
*A61B 6/03*    (2006.01)
*A61B 6/12*    (2006.01)
*A61B 6/00*    (2006.01)

(52) U.S. Cl.
CPC .............. *A61B 6/12* (2013.01); *A61B 6/037* (2013.01); *A61B 6/461* (2013.01); *A61B 6/481* (2013.01); *A61B 6/486* (2013.01); *A61B 6/5205* (2013.01)

(58) Field of Classification Search
CPC ......... A61B 6/481; A61B 6/037; A61B 6/486; A61B 6/461; A61B 6/5205
See application file for complete search history.

(56) References Cited

U.S. PATENT DOCUMENTS

| | | | |
|---|---|---|---|
| 2009/0256078 A1* | 10/2009 | Mazin | A61B 6/0407 250/362 |
| 2010/0316275 A1* | 12/2010 | Stolin | A61B 6/5264 382/131 |
| 2014/0228613 A1* | 8/2014 | Mazin | A61N 5/1039 600/1 |
| 2015/0355347 A1 | 12/2015 | Pratx | |
| 2018/0028079 A1* | 2/2018 | Gurevich | G06K 9/6218 |
| 2019/0362497 A1* | 11/2019 | Dwivedi | G06T 7/12 |

OTHER PUBLICATIONS

Lee, Keum Sil et al., "Single-Cell Tracking with PET using a Novel Trajectory Reconstruction Algorithm", Author Manuscript, IEEE Trans Med Imaging, Apr. 2015, vol. 34, Issue 4, DOI:10.1109/TMI.2014.2373351, (pp. 994-1003, 26 total pages).

(Continued)

*Primary Examiner* — David P Porta
*Assistant Examiner* — Mamadou Faye

(57) ABSTRACT

A system and method include acquisition of positron emission tomography data of an object while a radiation source moves within the object, determination of a plurality of locations within the object, each of the plurality of locations associated with a respective time at which the radiation source was located at the location, determination of a respective time period associated with each of the plurality of locations, determination, for each of the determined time periods, of a frame of the positron emission tomography data associated with the determined time period, and, for each frame of the positron emission tomography data, generation of an image based on the frame and on the location associated with the time period associated with the frame.

20 Claims, 6 Drawing Sheets

(56) References Cited

OTHER PUBLICATIONS

Jung, Kyung Oh et al., "CellGPS: Whole-body tracking of single cells by positron emission tomography", Aug. 24, 2019, https://doi.org/10.1101/745224, 35 pages.

Lecoq, Paul et al., "Case for setting up a 10 ps challenge: a step toward reconstruction-less TOF-PET", Jun. 11, 2019, https://the10ps-challenge-org/assets/img/10ps_motivation, 6 pages.

Jung et al, "Whole-body tracking of single cells via positron emission tomography," Nature Biomedical Engineering, Nature Publishing Group UK, London, vol. 4, No. 8, Jun. 15, 2020, pp. 835-844.

Gundogdu, O, "Positron Emission Tomography Particle tracking using cluster analysis," Nuclear Instruments & Methods in Physics Research, Section A, Elsevier BV, North-Holland NL, vol. 534, No. 3, Dec. 1, 2004, pp. 562-576.

International Search Report for Corresponding PCT Application No. PCT/US2021/070719, dated Sep. 24, 2021.

\* cited by examiner

RADIOLABELED CELL TRACKING AND IMAGING

BACKGROUND

According to conventional nuclear imaging, a radioactive tracer is first introduced into a patient body. The radioactive tracer emits gamma rays (in the case of single-photon-emission-computer-tomography (SPECT) imaging) or positrons which annihilate with electrons to produce gamma rays (in the case of positron-emission-tomography (PET) imaging). A detector system located outside the body detects the emitted gamma rays and reconstructs images based thereon.

For some medical applications, it is desirable to track the position of a single cell within the body. These applications may include tracking white blood cells to identify infection sites, tracking therapeutic cells used for tissue regeneration and cancer immunotherapy, and tracking cells involved in other biological processes. To track a cell using nuclear imaging, the cell is labeled with a radioactive tracer prior to introduction into the body.

The imaging paradigm presented by a radiolabeled cell is not suited for PET imaging. As the radiolabeled cell including a relatively small amount of radioactive tracer moves through the body, only sparse data of a small number of PET coincidence measurements is acquired. This sparse data is typically insufficient for conventional backprojection algorithms used for reconstructing PET images. As a result, PET images reconstructed based on the acquired data are not suitable for tracking the radiolabeled cell. Systems are desired to provide improved PET imaging of radiolabeled cells moving within a body.

DETAILED DESCRIPTION

The following description is provided to enable any person in the art to make and use the described embodiments and sets forth the best mode contemplated for carrying out the described embodiments. Various modifications, however, will remain apparent to those in the art.

Some embodiments provide generation of PET images based on PET data generated by a low-volume low-activity source moving through a body. Generally, locations of the source within the body at various timepoints are determined. PET data acquired during the motion is then framed based on the timepoints. A PET image is generated based on each frame by applying a point-source image generation algorithm to a frame in view of the source location associated with the timepoint represented in the frame. According to some embodiments, the locations of the source at the various timepoints may be determined based on known source motion, speed and behavior information, anatomical information and/or time-of-flight PET data. Accordingly, the locations are determined in some embodiments automatically and without the need for user input of the locations.

Embodiments may therefore provide improved PET images of various locations through which a low-volume low-activity source travels during PET imaging.

Figure 1:
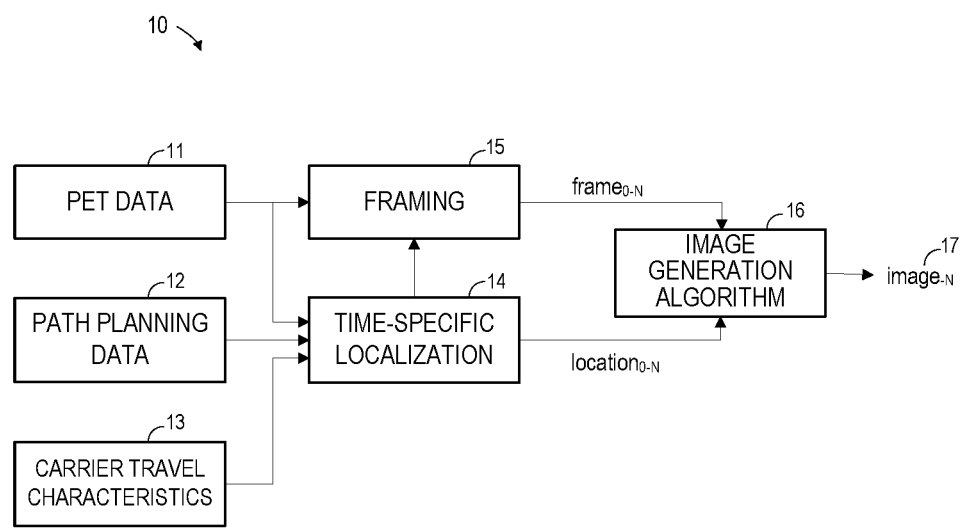
FIG. 1 is a block diagram of a system to generate images based on a low-activity low-volume source according to some embodiments.

FIG. 1 is a block diagram of system 10 according to some embodiments. System 10 may operate to generate a plurality of PET images 17 based on PET data 11. Generally, a small volume (e.g., a single cell or each cell of group of single cells) may be labeled with radioactive material (e.g., 1-10 Bq of radioactive 18Ffluorodeoxyglucose (FDG)) and injected into a body. The body is then scanned with a PET scanner over time to generate PET data 11.

Path planning data 12 may represent anatomical features of the body into which the small volume is injected. Path planning data 12 may be used as described below to assist in determining the course of travel of the small volume within the body over time. Path planning data 12 may be acquired using a different imaging modality than used to acquire PET data 11, either contemporaneously with acquisition of PET data 11 or not. Path planning data 12 may include assumptions regarding the anatomical features of the body.

Carrier travel characteristics 13 may include theoretical and/or experimentally-derived information associated with the expected movement of the volume through the body. Carrier travel characteristics 13 may specify an expected speed of the volume through the body, which may be a function of the type of volume, characteristics of the body fluids, and anatomical features indicated by path planning data 12. Together with path planning data 12, carrier travel characteristics 13 may assist a determination of where the volume is located at various times after injection into the body.

Time-specific localization component 14 estimates locations of the volume within the body over time based on PET data 11, path planning data 12 and carrier travel characteristics 13. Time-specific localization component 14 may use PET data 11, path planning data 12 and carrier travel characteristics 13 as boundary conditions of a determination of three-dimensional position of the volume over time. In this regard, PET data may include Time-of-Flight (TOF) information which provides positional information in addition to that provided by non-TOF PET data.

Time-specific localization component 14 provides three-dimensional locations of the volume at various times to framing component 15. Framing component 15 also receives PET data 11. Framing component 15 operates to generate frames of PET data associated with each of several three-dimensional locations. In some embodiments, a frame of PET data associated with a three-dimensional location includes PET data acquired from a particular time prior to the time at which the volume reached the location to a particular time after the time at which the volume reached the location.

The frames associated with the various positions (frame$_{0-N}$) and the associated locations (locations$_{0-N}$) are received by image generation algorithm 16. Using each frame (e.g., frame$_3$) and corresponding location (e.g., location$_3$), image generation algorithm 16 generates a corresponding PET image (e.g., image₃). Image generation algorithm 16 may comprise any suitable algorithm for generating a PET image based on sparse PET data and on a location of a low-volume source within the PET data. According to some embodiments, image generation algorithm 16 is a point source algorithm as is known in the art.

Each functional component of system 10 and of each other system described herein may be implemented in computer hardware, in program code and/or in one or more computing systems executing such program code as is known in the art. Each component may include any elements which are necessary for the operation thereof, as well as additional elements for providing functions other than those described herein. A computing system implementing one or more components may include one or more processing units which execute processor-executable program code stored in a memory system.

Figure 2:
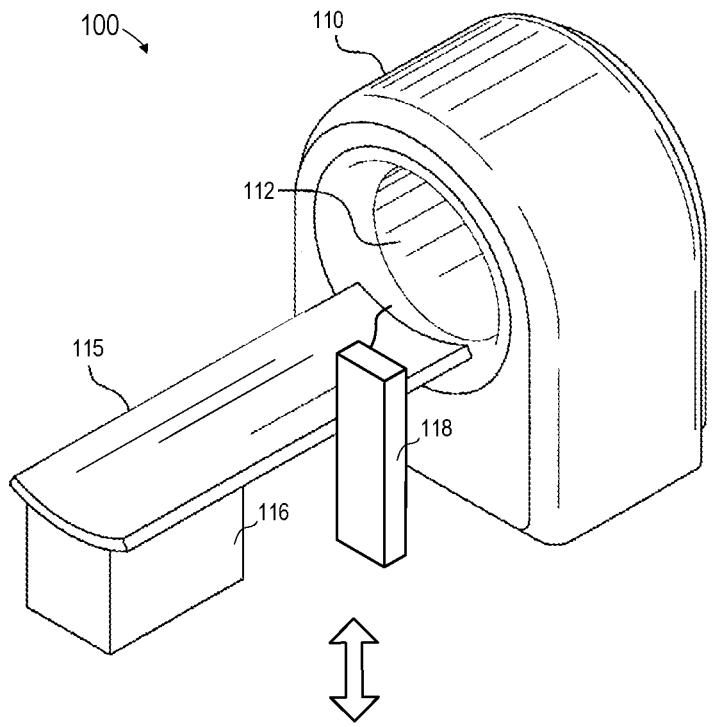
FIG. 2 is a block diagram of a PET/CT system to acquire PET data and to generate images based on the acquired PET data according to some embodiments.
Figure 2:
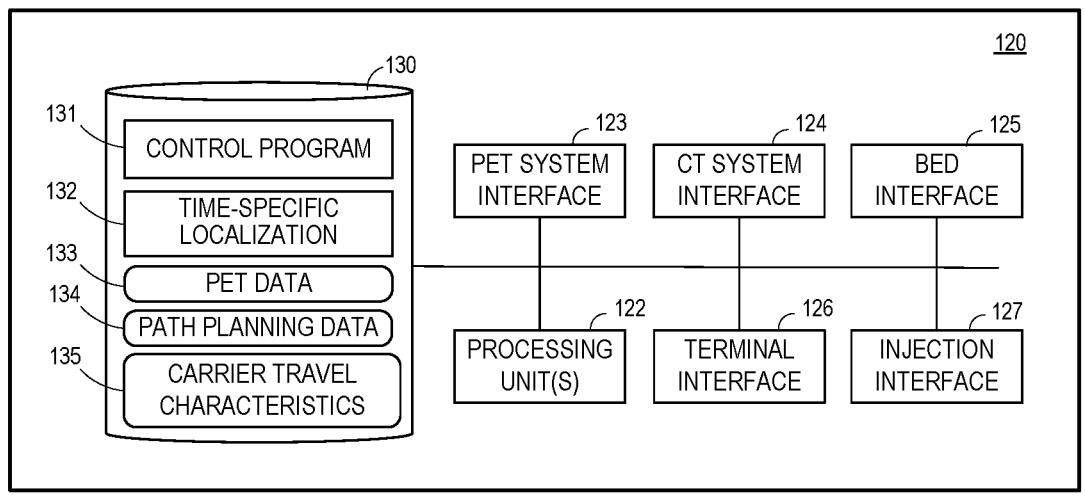
Figure 2:
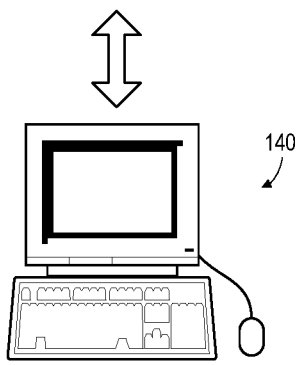

FIG. 2 illustrates PET/CT system 100 to execute one or more of the processes described herein. Embodiments are not limited to system 100.

According to conventional PET imaging, a tracer compound including a radionuclide or a radioactively-labeled cell(s) is introduced into a patient body by injection or ingestion. Radioactive decay generates positrons, which eventually encounter electrons and are annihilated thereby. Annihilation produces two gamma photons which travel in approximately opposite directions. Accordingly, an annihilation event, or prompt, is identified when two detectors disposed on opposite sides of the body detect the arrival of two oppositely-travelling gamma photons within a particular coincidence time window.

Because the two gamma photons travel in approximately opposite directions, the locations of the two detectors determine a Line-of-Response (LOR) along which the annihilation event occurred. Each annihilation event may be represented by raw (i.e., list-mode) data specifying the three-dimensional position and the time at which the event occurred. TOF PET additionally measures the difference between the detection times of the two gamma photons arising from the annihilation event. This difference may be used to estimate a particular position along the LOR at which the annihilation event occurred. As described above, this TOF-estimated position may be used to assist in localization of a low-volume source.

System 100 includes gantry 110 defining bore 112. As is known in the art, gantry 110 houses PET imaging components for acquiring PET image data and CT imaging components for acquiring CT image data. The CT imaging components may include one or more x-ray tubes and one or more corresponding x-ray detectors as is known in the art.

The PET imaging components may include any number or type of detectors (e.g., silicon photo-multipliers (SiPM) or photo-multiplier tubes (PMT) in any configuration as is known in the art. The detectors are associated with a slice thickness (spatial resolution) such that the components are capable of independently imaging two slices separated by a distance greater than or equal to the slice thickness. The slice thickness (e.g., 2.0 mm) corresponds to resolution of the detectors.

The CT imaging components may generate projection images of tissues indicating their relative x-ray attenuation coefficients. Three-dimensional CT images may be reconstructed based on these projection images as is known in the art. The three-dimensional CT images may comprise anatomical features used as path planning data to assist in localization of a low-volume source as described herein.

Injection system 118 may operate to deliver calibrated injections of one or more cells labeled with or tracer compound including FDG, iodine, or other radiopharmaceuticals to a patient before and/or during a PET scan. In some embodiments, injection system 118 is incorporated into gantry 110. Injection system 118 may support a wired or wireless communications link with control system 120 for receiving information specifying dosage, injection protocol and scan delay.

Bed 115 and base 116 are operable to move a patient lying on bed 115 into and out of bore 112 before, during and after imaging. In some embodiments, bed 115 is configured to translate over base 116 and, in other embodiments, base 116 is movable along with or alternatively from bed 115.

Movement of a patient into and out of bore 112 may allow scanning of the patient using the CT imaging elements and the PET imaging elements of gantry 110. Bed 115 and base 116 may provide continuous bed motion and/or step-and-shoot motion during such scanning according to some embodiments.

Control system 120 may comprise any general-purpose or dedicated computing system. Accordingly, control system 120 includes one or more processing units 122 configured to execute processor-executable program code to cause system 120 to operate as described herein, and storage device 130 for storing the program code. Storage device 130 may comprise one or more fixed disks, solid-state random-access memory, and/or removable media (e.g., a thumb drive) mounted in a corresponding interface (e.g., a USB port).

Storage device 130 stores program code of control program 131. One or more processing units 122 may execute control program 131 to, in conjunction with PET system interface 123, bed interface 125, and injection interface 127, control hardware elements to introduce a low-volume radiation source into a patient, place the patient into bore 112 surrounded by PET detectors of gantry 110, and detect coincidence events occurring within the patient. The detected events may be stored in memory 130 as PET data 133, which may comprise list-mode data and/or sinograms.

Control program 131 may also operate to frame PET data 133 based on estimated locations of a low-volume source over time and to generate PET images associated with each frame as described herein. In this regard, time-specific localization component 132 may be executed as described above to estimate the locations over time based on PET data 133 and stored path planning data 134 and carrier travel characteristics 135.

One or more processing units 122 may also execute control program 131 to, in conjunction with CT system interface 124, cause a radiation source within gantry 110 to emit radiation toward a body within bore 112 from different projection angles, and to control a corresponding detector to acquire two-dimensional CT data. The CT data may be acquired substantially contemporaneously with the PET data.

Generated PET images and/or CT images may be transmitted to terminal 140 via terminal interface 126. Terminal 140 may comprise a display device and an input device coupled to system 120 to display the PET images. Terminal 140 may receive user input for controlling display of the data, operation of system 100, and/or the processing described herein. In some embodiments, terminal 140 is a separate computing device such as, but not limited to, a desktop computer, a laptop computer, a tablet computer, and a smartphone.

Figure 3:
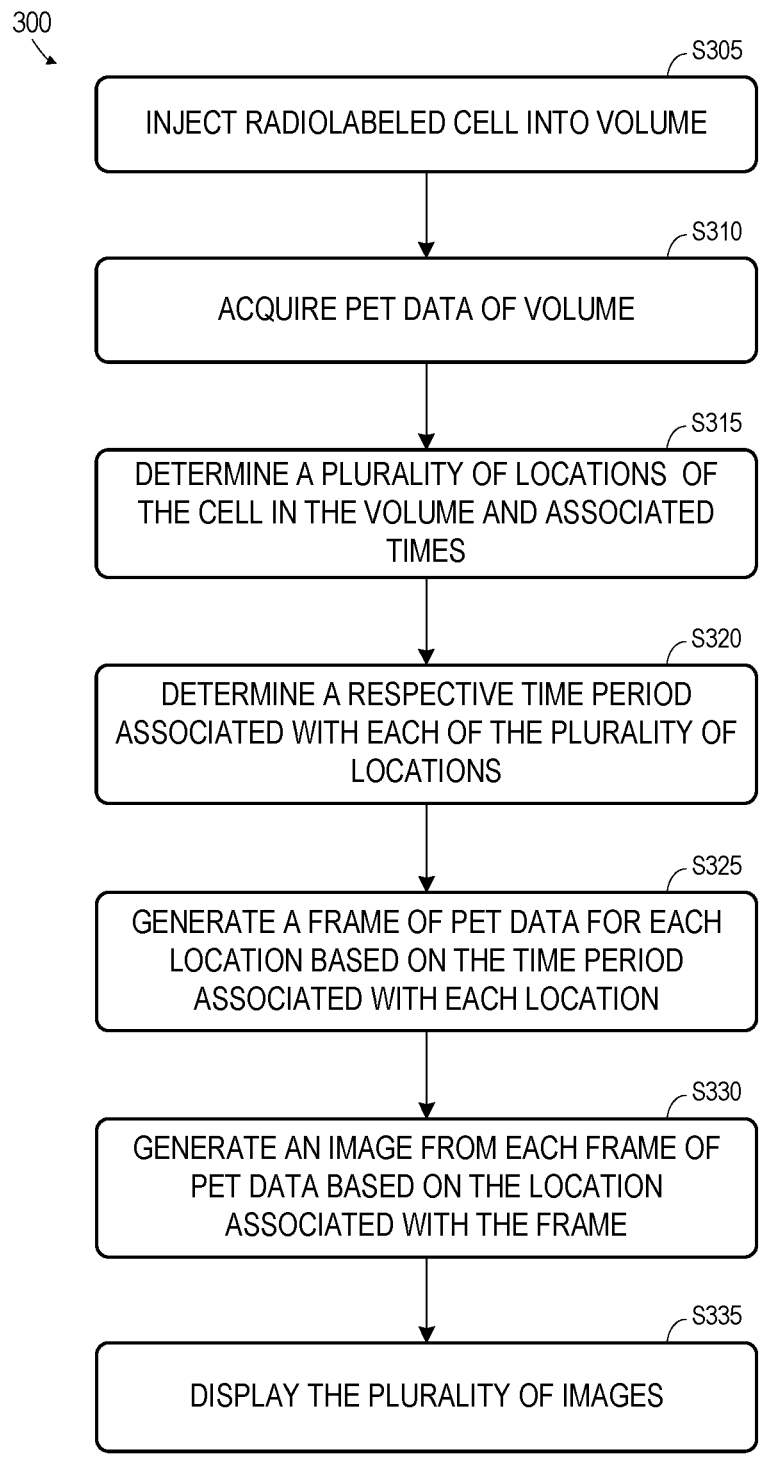
FIG. 3 comprises a flow diagram of a process to generate images based on a low-activity low-volume source according to some embodiments.

FIG. 3 comprises a flow diagram of process 300 to generate PET images according to some embodiments. Flow diagram 300 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape. Embodiments are not limited to the examples described below.

A radiolabeled cell is initially injected into an object (e.g., a patient) at S305. Radiolabelling of the cell may occur in any suitable manner that is or becomes known. The cell may comprise any suitable cell type and the radiolabel may comprise any suitable compound. In some embodiments, more than one radiolabeled cell is injected at S305.

After injection, PET data of the object is acquired at S310. The PET data may be acquired by a conventional static PET scan after injection of the radiolabeled cell into as is known in the art. The acquired PET data may comprise, in some embodiments, list-mode PET data as described above. The PET data may be acquired by an imaging system separate from a system which performs the remaining steps of process 300. For example, the PET data may be originally acquired in an imaging theatre, with the remaining steps of process 300 being executed by a separate system in a separate location hours, days, months, etc. after the acquisition.

According to some embodiments, the data acquired at S310 by a PET scanner is formatted into sinograms. A sinogram is a data array of the angle versus the displacement of each LOR. Each sinogram stores the location of the LOR of each coincidence event such that all the LORs passing through a single point in the imaged object trace a sinusoid curve in the sinogram. Each sinogram includes one row containing the LOR for a particular azimuthal angle φ. Each of such rows corresponds to a one-dimensional parallel projection of the tracer compound distribution at a different coordinate.

At S315, a plurality of locations of the injected cell over time are determined. As described above, the locations of may be determined based on the acquired PET data, path planning data (e.g., acquired by a contemporaneous CT scan) and known carrier travel characteristics. For example, the determination at S315 may be based on boundary conditions defined by TOF data which provides estimated annihilation locations at specific times, and on travel characteristics and anatomical features which limit the solution space for a given time. Each location determined at S315 is therefore associated with a time at which the cell was present at the location.

Figure 4:
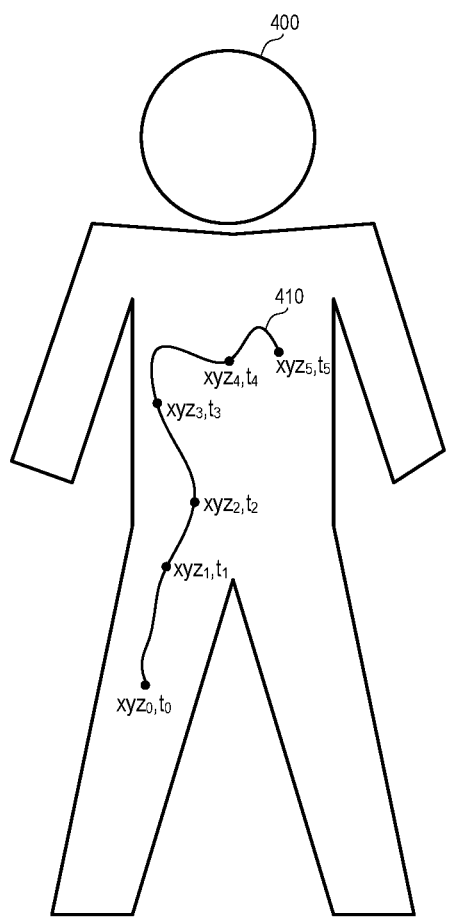
FIG. 4 illustrates a path of a low-volume radiation source within a body according to some embodiments.

FIG. 4 illustrates travel of a low-volume radiation source through body 400 over time. Path 410 indicates an injection location $xyz_0$ and an associated injection time to (i.e., a time at which the low-volume radiation source was located at location $xyz_0$), and various other locations and associated times until an end of path 410 at location $xyz_5$, which is associated with time $t_4$. The six indicated locations of path 410 may be determined at S315 as described above, but embodiments are not limited to any particular number of determined locations.

At S320, a respective time period is determined for each of the determined locations. The respective time period determined for a particular location is a time period surrounding the time which is associated with the location (i.e., the time at which the source is determined to be present at the location). The length of the time periods associated with the determined locations need not be equal. The time period determined for a location may be determined so as collect sufficient PET data as the source approaches and moves away from the location. In this regard, a frame of the acquired PET data is generated at S325 for each location based on the time period associated with the location.

Figure 5:
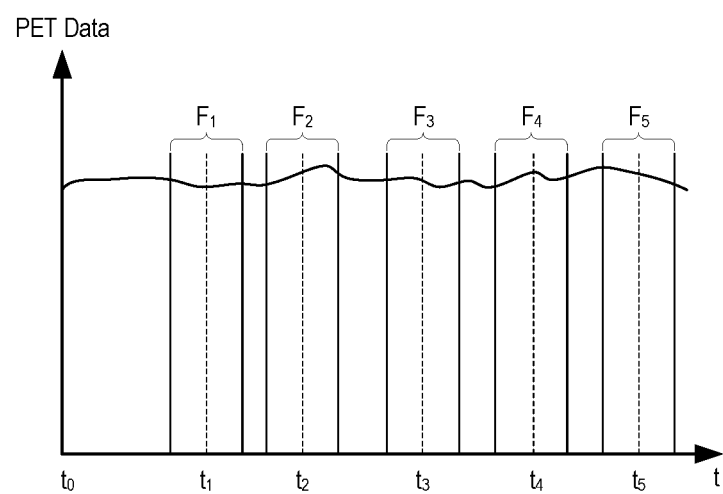
FIG. 5 illustrates framing of acquired PET data based on determined locations of a low-volume radiation source over time according to some embodiments.

FIG. 5 illustrates S320 and S325 according to some embodiments. FIG. 5 is a plot of received PET data (e.g., represented as counts acquired at a given time) over time. Each of times $t_1$ through $t_5$ is associated with a corresponding determined location $xyz_1$ through $xyz_5$. Each of times $t_1$ through $t_5$ is shown in conjunction with two solid lines and a bracket illustrating a respective time period determined at S320. As shown, the time period associated with a given one of times $t_1$ through $t_5$ defines a portion of the PET data which was acquired during the time period. This portion is used to generate a frame of PET data for the corresponding time and location. For example, $F_1$ is a frame of PET data corresponding to time $t_1$ and location $xyz_1$.

An image is generated from each frame of PET data at S330 based on the location associated with the frame. As noted above, a point-source algorithm may generate an image based on sparse PET data and on a location of a radiation source. Accordingly, S330 may comprise inputting a frame of PET data generated at S325 (e.g., Frame $F_1$) and a corresponding location (e.g., $xyz_1$) to a point source algorithm.

Figure 6:
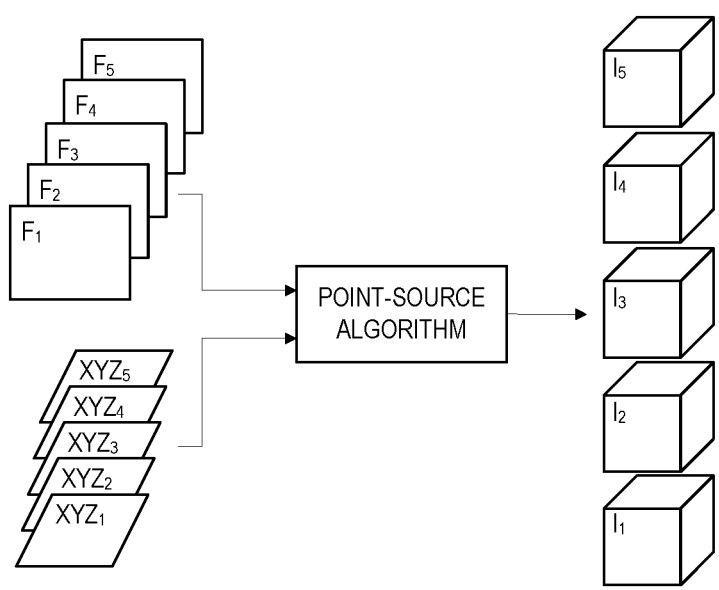
FIG. 6 illustrates generation of PET images based on determined source locations and frames of PET data associated with the determined source locations according to some embodiments.

FIG. 6 illustrates S330 according to some embodiments. As shown, a point-source algorithm receives frames $F_1$ through $F_5$ of PET data and corresponding location data $xyz_1$ through $xyz_5$. Using each frame and corresponding location, the point-source algorithm generates a corresponding three-dimensional PET image $I_1$ through $I_5$.

The plurality of images may be displayed at S335. Each image represents activity at locations surrounding the location corresponding to the image, and therefore represent three-dimensional areas along the path of the source. The images may be displayed in a time-lapse and/or "fly-through" sequence according to some embodiments.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
   an imaging device to:
      acquire positron emission tomography data associated with a radiation source within an object; and
   a processing system to:
      determine a plurality of locations within the object, and, for each of the plurality of locations, a respective time at which the radiation source was located at the location, wherein the plurality of locations are determined without user input of the plurality of locations;
      determine a respective time period associated with each of the plurality of locations, based on the respective time at which the radiation source was located at the location;
      determine, for each of the determined time periods, a frame of the positron emission tomography data acquired during the determined time period;
      for each frame of the positron emission tomography data, generate an image of the object based on the frame and on the location associated with the time period associated with the frame; and
      display the images.

2. A system according to claim 1, wherein the radiation source is a radiolabeled cell.

3. A system according to claim 1, wherein generation of an image comprises execution of a point-source algorithm with respect to a frame of the positron emission tomography data and a location associated with a time period associated with the frame.

4. A system according to claim 1, wherein determination of the plurality of locations within the object comprises:
determination of the plurality of locations based on anatomical features of the object and on travel characteristics of the radiation source.

5. A system according to claim 4, wherein determination of the plurality of locations within the object comprises:
determination of the plurality of locations based on anatomical features of the object, on travel characteristics of the radiation source, and on the positron emission tomography data,
wherein the positron emission tomography data comprises Time-of-Flight positron emission tomography data.

6. A system according to claim 5, wherein the radiation source is a radiolabeled cell.

7. A system according to claim 6, wherein generation of an image comprises execution of a point-source algorithm with respect to a frame of the positron emission tomography data and a location associated with a time period associated with the frame.

8. A method comprising:
injecting a radiation source into an object;
acquiring positron emission tomography data of the object while the radiation source moves within the object;
determining a plurality of locations within the object and, for each of the plurality of locations, a respective time at which the radiation source was located at the location;
determining a respective time period associated with each of the plurality of locations, based on the respective time at which the radiation source was located at the location;
determining, for each of the determined time periods, a frame of the positron emission tomography data acquired during the determined time period; and
for each frame of the positron emission tomography data, generating an image of the object based on the frame and on the location associated with the time period associated with the frame.

9. A method according to claim 8, wherein the radiation source is a radiolabeled cell.

10. A method according to claim 8, wherein generating an image comprises executing a point-source algorithm with respect to a frame of the positron emission tomography data and a location associated with a time period associated with the frame.

11. A method according to claim 8, wherein determining the plurality of locations within the object comprises:
determining the plurality of locations based on anatomical features of the object and on travel characteristics of the radiation source.

12. A method according to claim 11, wherein determining the plurality of locations within the object comprises:
determining the plurality of locations based on anatomical features of the object, on travel characteristics of the radiation source, and on the positron emission tomography data,
wherein the positron emission tomography data comprises Time-of-Flight positron emission tomography data.

13. A method according to claim 12, wherein the radiation source is a radiolabeled cell.

14. A method according to claim 13, wherein generating an image comprises executing a point-source algorithm with respect to a frame of the positron emission tomography data and a location associated with a time period associated with the frame.

15. A computing system comprising:
a memory storing processor-executable process steps; and
a processing unit to execute the processor-executable process steps to:
acquire positron emission tomography data of an object while a radiation source moves within the object;
determine a plurality of locations within the object and, for each of the plurality of locations, a respective time at which the radiation source was located at the location;
determine a respective time period associated with each of the plurality of locations, based on the respective time at which the radiation source was located at the location;
determine, for each of the determined time periods, a frame of the positron emission tomography data acquired during the determined time period; and
for each frame of the positron emission tomography data, generate an image of the object based on the frame and on the location associated with the time period associated with the frame.

16. A system according to claim 15, wherein the radiation source is a radiolabeled cell.

17. A system according to claim 15, wherein generation of an image comprises execution of a point-source algorithm with respect to a frame of the positron emission tomography data and a location associated with a time period associated with the frame.

18. A system according to claim 15, wherein determination of the plurality of locations within the object comprises:
determination of the plurality of locations based on anatomical features of the object and on travel characteristics of the radiation source.

19. A system according to claim 18, wherein determination of the plurality of locations within the object comprises:
determination of the plurality of locations based on anatomical features of the object, on travel characteristics of the radiation source, and on the positron emission tomography data,
wherein the positron emission tomography data comprises Time-of-Flight positron emission tomography data.

20. A system according to claim 19, wherein generation of an image comprises executing a point-source algorithm with respect to a frame of the positron emission tomography data and a location associated with a time period associated with the frame.

* * * * *